(12) United States Patent
Bourque et al.

(10) Patent No.: US 9,545,261 B2
(45) Date of Patent: Jan. 17, 2017

(54) INSTRUMENT GUIDE

(75) Inventors: Bernard Joseph Bourque, Rehoboth, MA (US); Michael Charles Ferragamo, Foster, RI (US); Steve Bernard Reynolds, Attleboro, MA (US)

(73) Assignee: Smith & Nephew, Inc., Memphis, TN (US)

( * ) Notice: Subject to any disclaimer, the term of this patent is extended or adjusted under 35 U.S.C. 154(b) by 176 days.

(21) Appl. No.: 13/348,877

(22) Filed: Jan. 12, 2012

(65) Prior Publication Data

US 2013/0184610 A1    Jul. 18, 2013

Related U.S. Application Data

(60) Provisional application No. 61/513,320, filed on Jul. 29, 2011.

(51) Int. Cl.

| A61B 5/00 | (2006.01) |
|---|---|
| A61B 17/17 | (2006.01) |
| A61B 17/34 | (2006.01) |
| A61B 17/29 | (2006.01) |
| A61B 17/16 | (2006.01) |

(52) U.S. Cl.
CPC ....... *A61B 17/1796* (2013.01); *A61B 17/1714* (2013.01); *A61B 17/1764* (2013.01); *A61B 17/3403* (2013.01); *A61B 17/1697* (2013.01); *A61B 2017/2927* (2013.01); *A61B 2017/3405* (2013.01)

(58) Field of Classification Search
CPC .................. A61M 25/09; A61M 2025/09175; A61M 2025/09083
USPC .......................... 600/585; 604/264, 508, 523
See application file for complete search history.

(56) References Cited

U.S. PATENT DOCUMENTS

| 4,712,545 A | 12/1987 | Honkanen |
|---|---|---|
| 4,758,035 A | 7/1988 | Shimasaki |
| 5,643,273 A | 7/1997 | Clark |
| 6,322,565 B1 | 11/2001 | Garner et al. |
| 7,682,319 B2 * | 3/2010 | Martin et al. .................. 600/585 |

(Continued)

FOREIGN PATENT DOCUMENTS

| DE | 202005020819 U1 | 9/2006 |
|---|---|---|
| DE | 102010013459 B3 | 6/2011 |

(Continued)

OTHER PUBLICATIONS

International Search Report and Written Opinion for International Application No. PCT/US2012/048650, mailed Oct. 18, 2012.

(Continued)

*Primary Examiner* — Daniel Cerioni

(57) ABSTRACT

A guide for a flexible member includes a stationary member, an articulating member, and an actuating member. The articulating member defines a first lumen. The stationary member, the articulating member, and the actuating member are coupled to one another by one or more arcuate grooves or flanges such that the articulating member pivots relative to the stationary member when the actuating member is moved relative to the stationary member. The stationary member and the actuating member form a second lumen arranged to accommodate the flexible member coextensively in the first lumen and the second lumen.

12 Claims, 15 Drawing Sheets

(56) References Cited

U.S. PATENT DOCUMENTS

| | | | |
|---|---|---|---|
| 7,881,809 B2* | 2/2011 | Rashidi | 607/122 |
| 7,963,963 B2* | 6/2011 | Francischelli et al. | 606/51 |
| 8,123,703 B2* | 2/2012 | Martin et al. | 600/585 |
| 8,182,467 B2* | 5/2012 | Nguyen et al. | 604/528 |
| 2003/0020292 A1 | 1/2003 | Hsu | |
| 2004/0054322 A1* | 3/2004 | Vargas | 604/95.04 |
| 2007/0123889 A1 | 5/2007 | Malandain et al. | |
| 2007/0270679 A1* | 11/2007 | Nguyen et al. | 600/373 |
| 2008/0097391 A1* | 4/2008 | Feinberg et al. | 604/523 |
| 2008/0114364 A1 | 5/2008 | Goldin et al. | |
| 2008/0294167 A1 | 11/2008 | Schumacher et al. | |
| 2009/0116606 A1 | 5/2009 | Lee et al. | |
| 2009/0157081 A1 | 6/2009 | Homan et al. | |
| 2009/0163934 A1* | 6/2009 | Raschdorf et al. | 606/139 |
| 2009/0171147 A1* | 7/2009 | Lee et al. | 600/104 |
| 2010/0057087 A1 | 3/2010 | Cha | |
| 2010/0298832 A1 | 11/2010 | Lau et al. | |
| 2011/0015674 A1 | 1/2011 | Howard et al. | |

FOREIGN PATENT DOCUMENTS

| | | |
|---|---|---|
| EP | 2005905 B1 | 12/2008 |
| EP | 2072015 A2 | 6/2009 |
| NL | 1009471 C2 | 12/1999 |
| WO | WO2010059227 A1 | 5/2010 |

OTHER PUBLICATIONS

Australian Patent Application No. 2012290297, Patent Examination Report No. 1, mailed Feb. 12, 2016 (D1 previously cited).

Office Action for Japanese Application No. 2014-523084, mailed on Jun. 27, 2016.

Office Action for Russian Patent Application No. 2014106900/14(010941), mailed on Apr. 20, 2016.

Office Action for Chinese Patent Application No. 201280047695.8, mailed on Aug. 30, 2016.

* cited by examiner

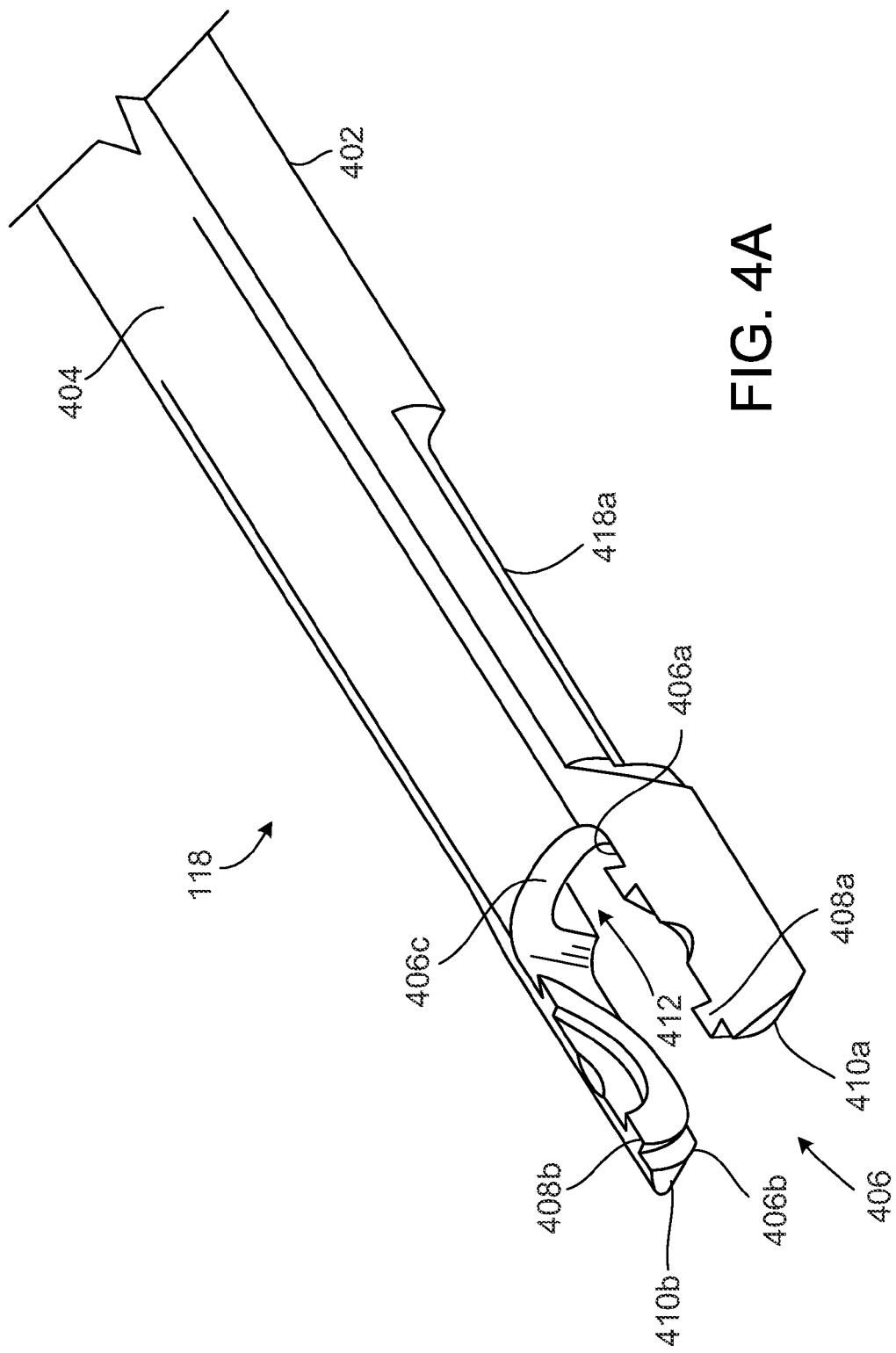

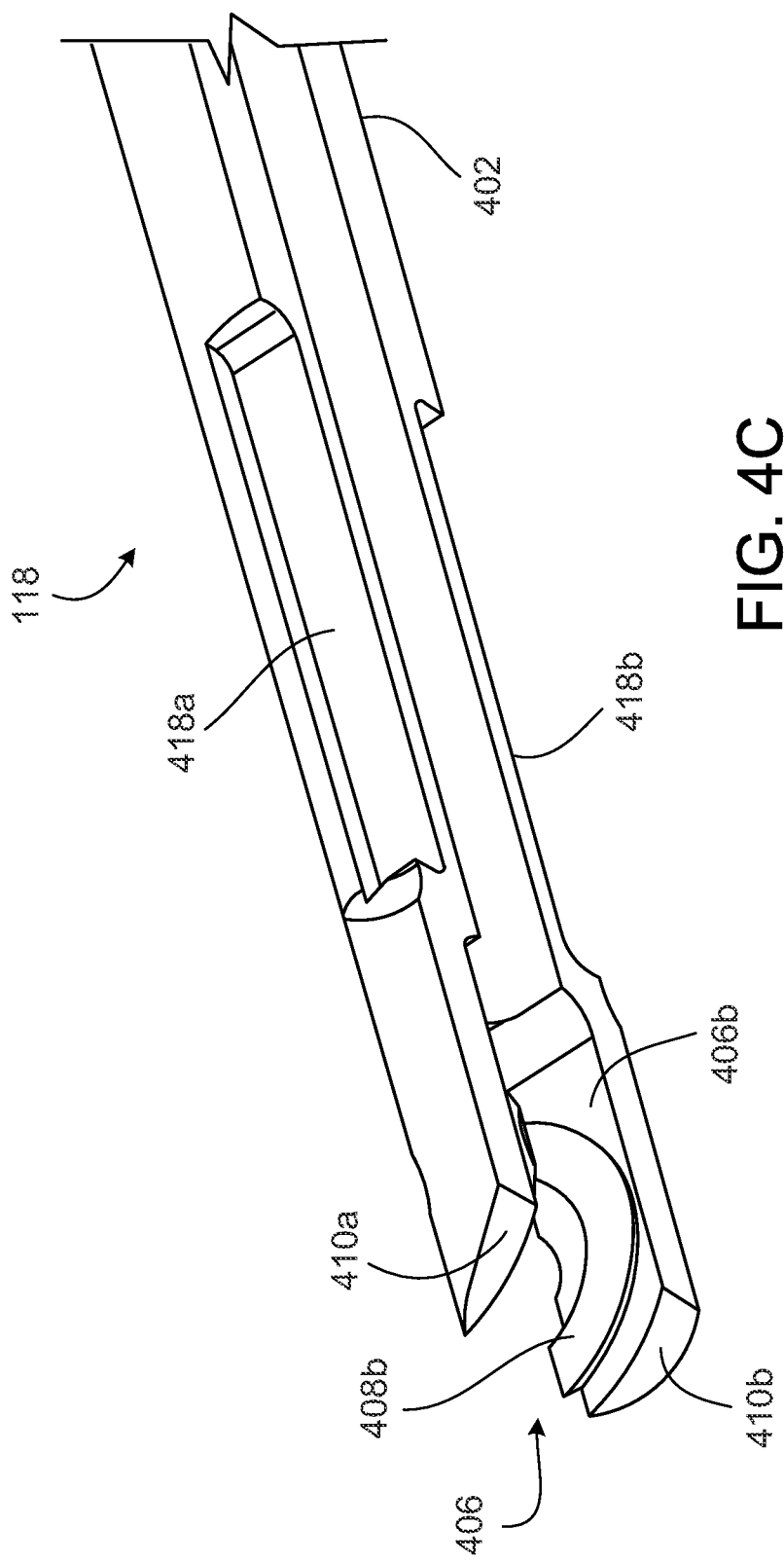

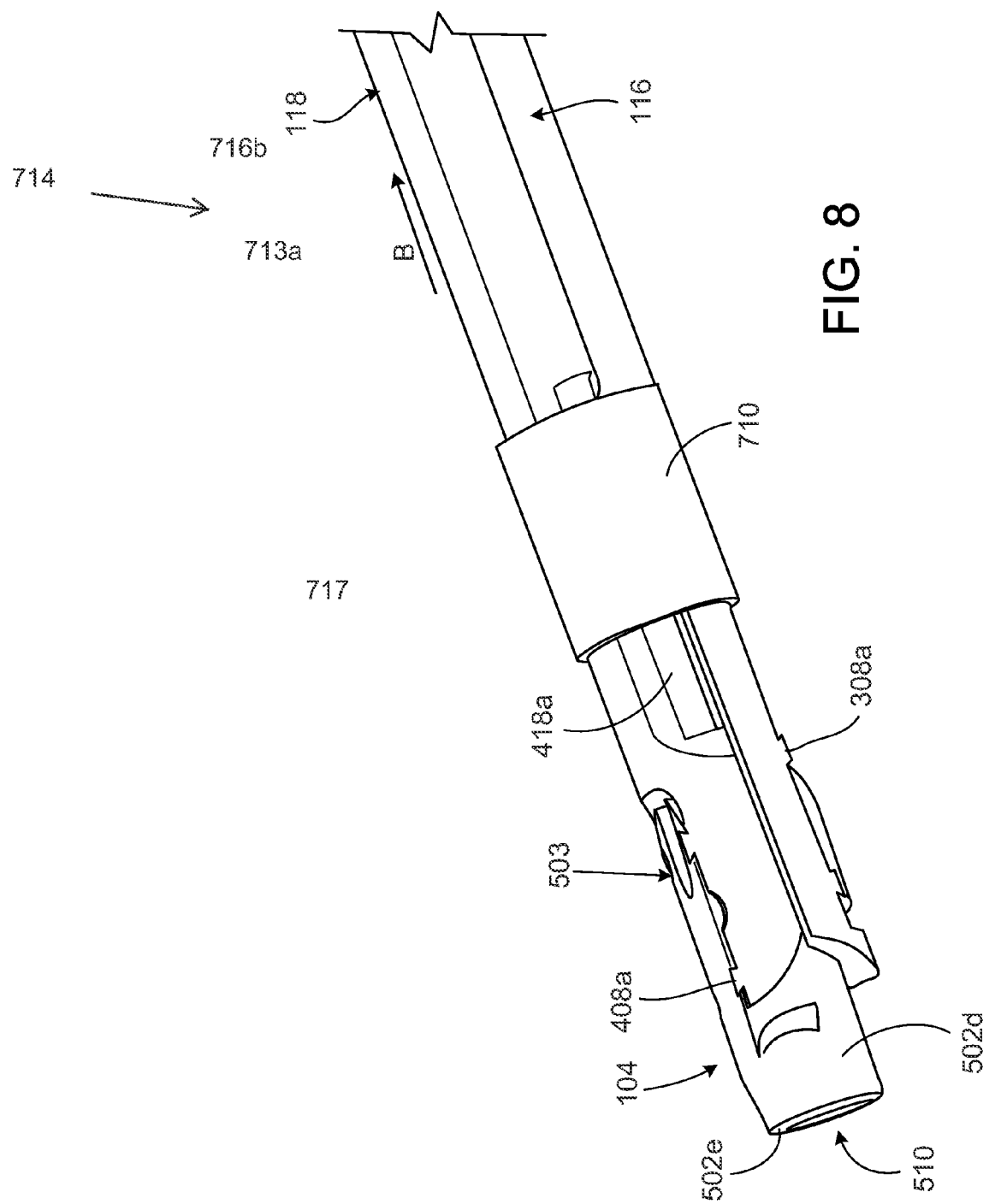

INSTRUMENT GUIDE

CROSS-REFERENCE TO RELATED APPLICATIONS

Under 35 U.S.C. §119 (e)(1), this application claims benefit of prior U.S. provisional application 61/513,320, filed Jul. 29, 2011.

TECHNICAL FIELD

This disclosure relates to surgical guides.

BACKGROUND

Some surgical procedures involve forming passages in bone. For instance, an anterior cruciate ligament (ACL) that has ruptured and is non-repairable can be replaced arthroscopically by a tissue graft. The replacement tissue graft can be implanted by securing one end of the tissue graft in a socket formed in a passage within the femur, and passing the other end of the graft through a passage formed in the tibia.

SUMMARY

In one aspect, a guide for a flexible member includes a stationary member, an articulating member, and an actuating member. The articulating member defines a first lumen. The stationary member, the articulating member, and the actuating member are coupled to one another by one or more arcuate grooves or flanges such that the articulating member pivots relative to the stationary member when the actuating member is moved relative to the stationary member. The stationary member and the actuating member form a second lumen arranged to accommodate the flexible member coextensively in the first lumen and the second lumen.

Implementations may include one or more of the following features. The stationary member, the articulating member, and the actuating member may be coupled such that the first lumen and the second lumen are coaxially arranged when the actuating member is in a first position relative to the stationary member and are non-coaxially arranged when the actuating member is in a second position relative to the stationary member.

The stationary member may include a first arcuate groove or flange. The articulating member may include a lower extension portion that includes a second arcuate groove or flange coupled to the first arcuate grove or flange. The lower extension portion may be received in a slot in the stationary member.

The articulating member may include a first arcuate groove or flange. The articulating member may also include an upper portion that includes a second arcuate groove or flange coupled to the first arcuate groove or flange. The lower extension portion may be received in a slot in the stationary member.

The articulating member may include a main body member with a first arcuate groove formed in an upper portion of the main body member, the first arcuate groove coupled to a first arcuate flange on the actuating member. The articulating member may also include a lower extension portion which is coupled to a lower portion of the main body. The lower extension portion may be received in a slot of the stationary member. The lower extension portion may also include a second arcuate groove coupled to an arcuate flange formed in the slot.

The handle may be coupled to the stationary member and the actuating member such that operation of the handle causes the actuating member to move relative to the stationary member.

The handle may include a first member coupled to the actuating member and a second member coupled to the stationary member. The first member and the second member may be coupled such that the first member rotates relative to the second member to move the actuating member.

The handle may comprise a pin. The pin couples the first member and the second member such that the first member rotates relative to the second member.

The handle may also include a ratchet mechanism that allows the first member to rotate in one direction and prevents the first member from rotating in a second direction, opposite the first direction. Rotation of the first member in the first direction moves the actuating member from the first position to the second position.

The ratchet mechanism may include one or more teeth on the second member and a finger on the first member. The finger may be configured to engage the teeth. The finger may be configured to move in a first direction to engage the teeth and to move in a second direction to disengage the teeth. The ratchet mechanism may include a spring configured to apply a force to the finger in the first direction to engage with the teeth and allow the finger to be moved in the second direction to disengage the finger from the teeth.

In another aspect, a medical device includes a stationary member, an articulating member, and an actuating member. The stationary member has a distal region and a proximal region. The articulating member defines a first lumen, and the stationary member and the actuating member form a second lumen. A flexible member is arranged coextensively in the first lumen and the second lumen. The stationary member, the articulating member, and the actuating member are coupled to one another by one or more arcuate grooves or flanges such that the articulating member pivots relative to the stationary member when the actuating member is moved relative to the stationary member. The articulating member pivoting relative to the stationary member causes the flexible member to change from a substantially straight configuration to a bent configuration.

The details of one or more implementations are set forth in the accompanying drawings and the description below. Other features, aspects, and advantages will become apparent from the description, the drawings, and the claims.

BRIEF DESCRIPTION OF THE DRAWINGS

FIG. 4A is a perspective view of the distal end of an actuating member of the surgical guide.

FIG. 4C is a perspective view of the distal end of an actuating member of the surgical guide.

FIG. 8 is a perspective view of the distal end of the surgical guide.

DETAILED DESCRIPTION

Figure 1A:
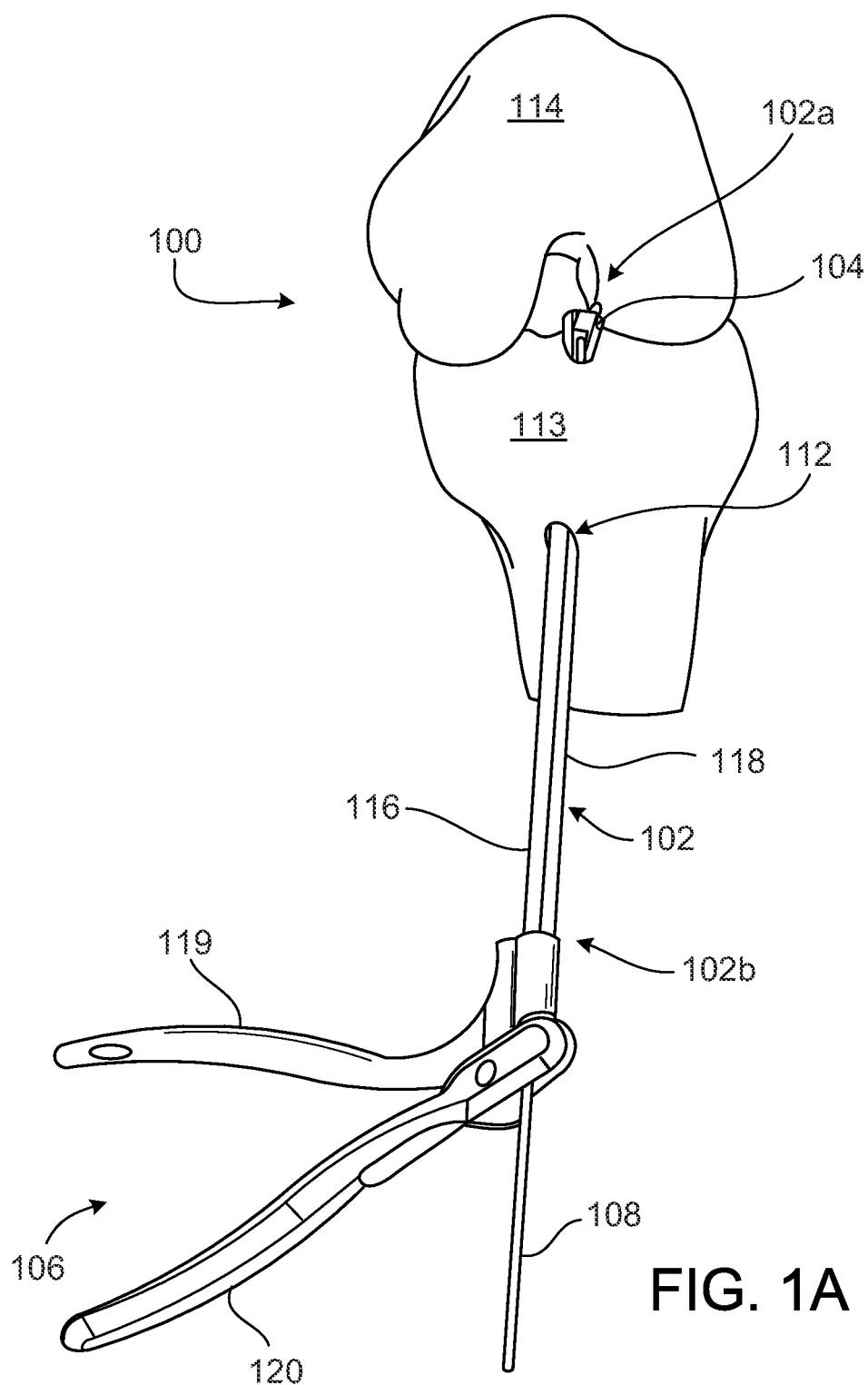
FIG. 1A is a plan view of a knee joint with a surgical guide.
Figure 1B:
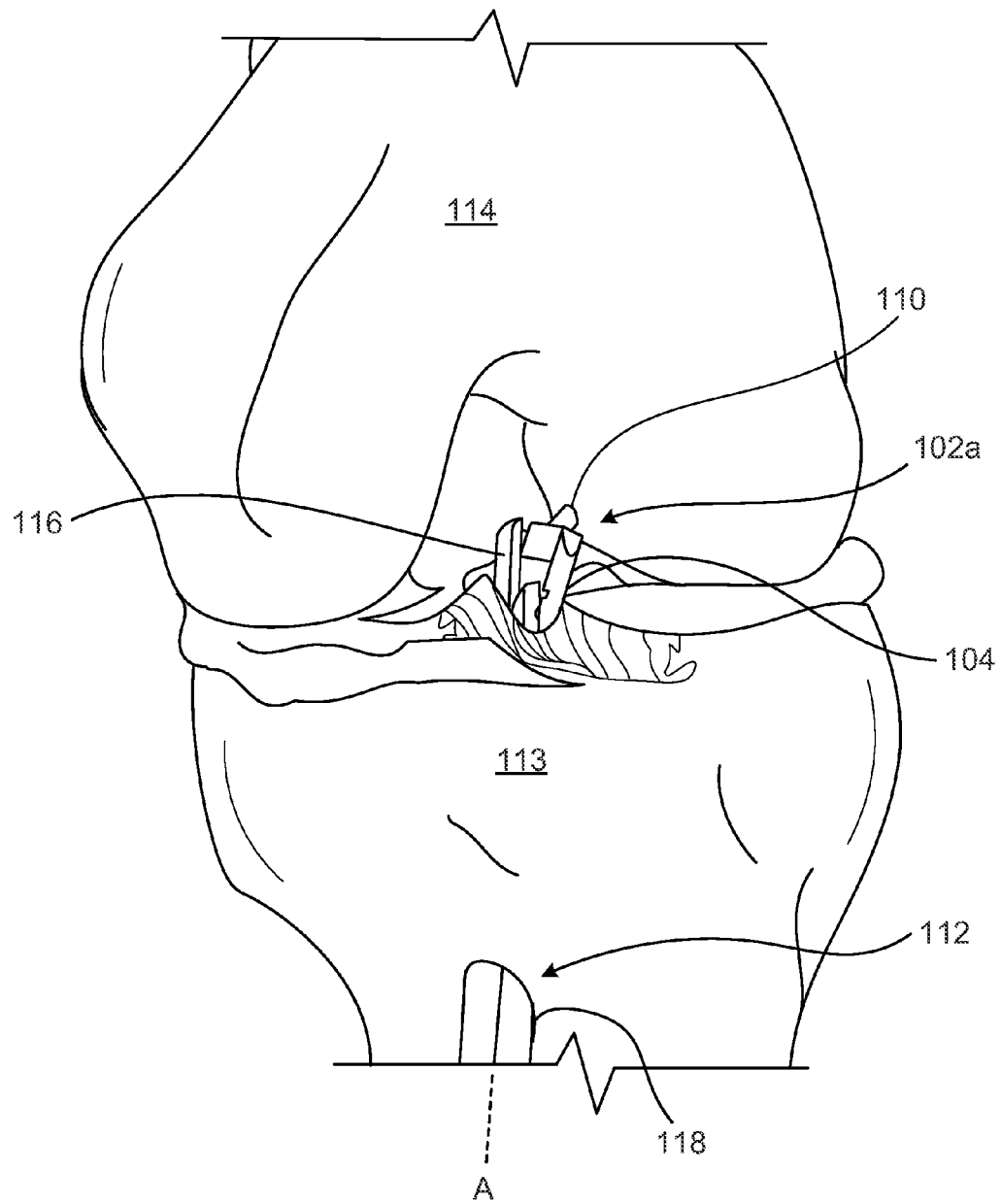
FIG. 1B is a plan view of a knee joint and the tip of the surgical guide.

FIGS. 1A and 1B illustrate an example of a surgical guide, such as a flexible pin guide 100, being used, for example, during an anterior cruciate ligament (ACL) surgery. The flexible pin guide 100 includes an elongated shaft 102 that includes a distal end 102a and a proximal end 102b. The distal end 102a includes an articulating member 104 and the proximal end 102b of the shaft 102 is coupled to a scissors-type handle 106. A flexible member 108, otherwise referred to as a guide wire or passing pin, passes through a lumen in the shaft 102 and a distal end 110 of the pin 108 extends out of an opening in the articulating member 104. Through use of the handle 106, the articulating member 104 can be pivoted relative to a longitudinal axis, A, of the shaft 102.

When used during an ACL surgery, the surgeon forms a tunnel 112 in the tibia 113 and passes the elongated shaft 102 through the tibial tunnel 112 such that the distal end 102a of the shaft 102 exits an opening in the end of the tibial tunnel 112 and enters the knee joint. The surgeon operates the handle 106, which results in the articulating member 104 pivoting relative to the longitudinal axis A, which corresponds to the longitudinal axis of the tibial tunnel 112. Pivoting the articulating member 104 results in the pin 108 bending, this allows the distal end 110 of the pin 108 to engage the lateral condyle of the femur 114 at an angle relative to the longitudinal axis A of the tibial tunnel 112. The pin 108 is then drilled or otherwise passed through the lateral condyle and used as a guide for a flexible drill, which is used to drill a tunnel through the lateral condyle of the femur 114. The resulting femoral tunnel has a longitudinal axis that is at an angle to the longitudinal axis A of the tibial tunnel 112.

An angled femoral tunnel may provide an ACL repair that is more anatomically correct than one in which the femoral and tibial tunnels are not angled with respect to each other. With the knee flexed to 90 degrees, using the flexible pin guide 100 may allow a surgeon to create an angled femoral tunnel without the need for an additional portal, such as an anteromedial portal. Further, some surgeons may be trained using a transtibial approach, and using the flexible pin guide may allow them to continue this approach, but create a more anatomically correct repair relative to one in which the femoral tunnel is aligned with the tibial tunnel.

Figure 2A:
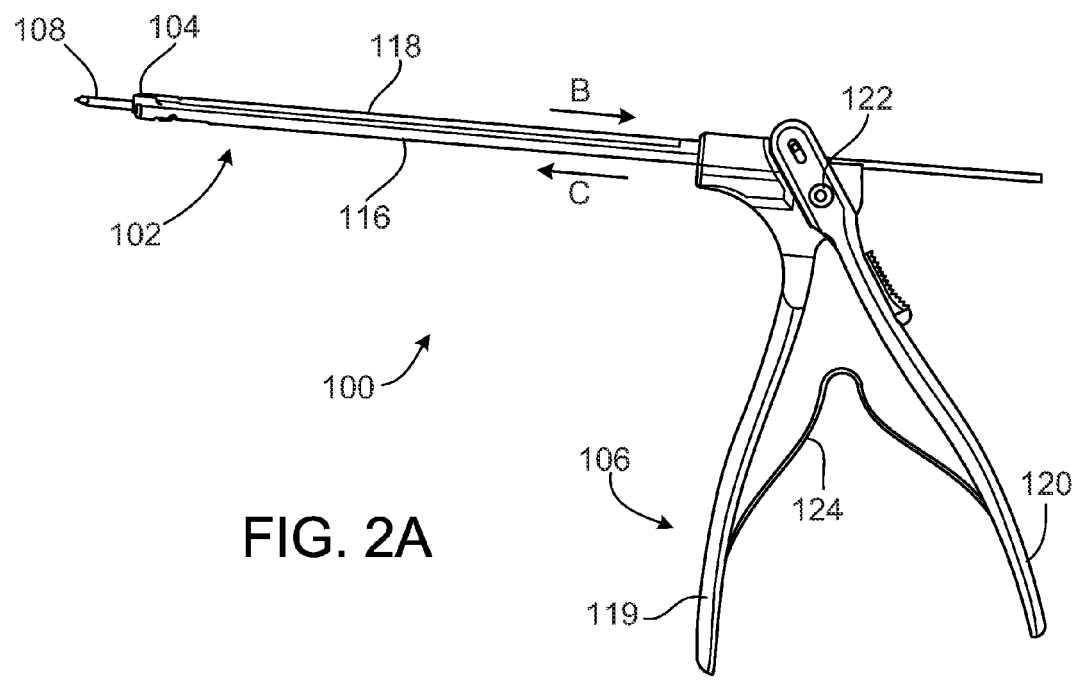
FIGS. 2A and 2B are plan views of the surgical guide and a guide wire
Figure 2B:
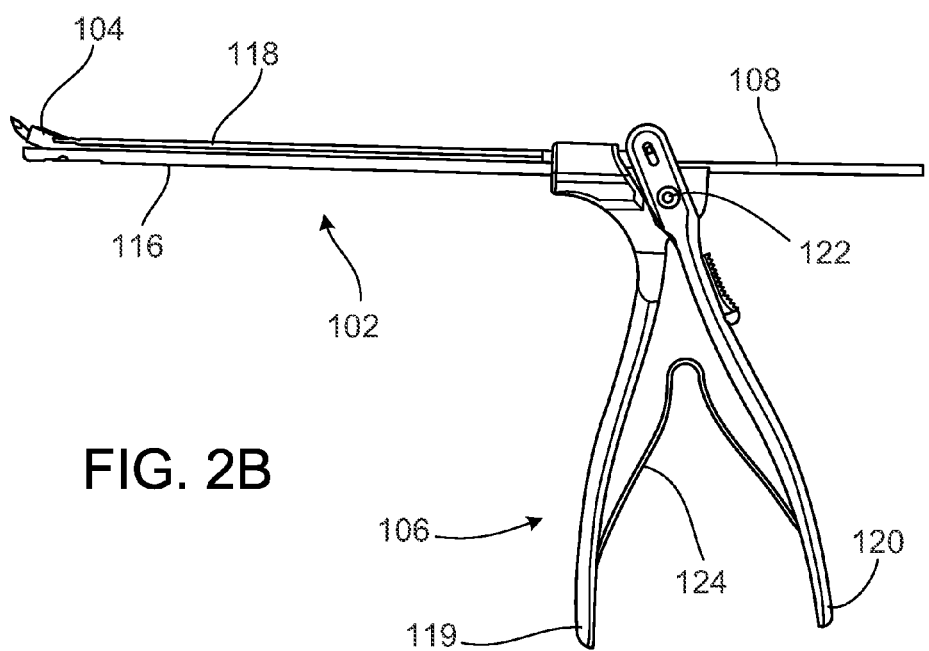

Referring also to FIGS. 2A and 2B, in more detail, the elongated shaft 102 includes a stationary member 116, an actuating member 118, and an articulating member 104, which functions as the articulating tip. The handle 106 includes a stationary handle member 119 coupled to an articulating handle member 120 by a pin 122 such that the articulating handle member 120 pivots relative to the stationary handle member 119 about an axis of the pin 122. A flat spring 124 is positioned between the handle members 119 and 120 to provide a force that tends to separate the handle members 119 and 120 so that the handles 119 and 120 tend to move to their open position. The stationary member 116 is coupled to the stationary handle member 119, while the actuating member 118 is coupled to the articulating handle member 120.

When the handle members 119 and 120 are in their open position, the articulating member 104 is in a first, non-pivoted position, as shown in FIG. 2A. As the articulating handle member 120 is rotated relative to the stationary handle member 119 about pin 122 (for example, by a surgeon squeezing the handles 119 and 120), the actuating member 118 moves relative to the stationary member 116 in the direction of arrow B. As discussed in more detail below, the stationary member 116, the actuating member 118, and the articulating member 104 are coupled by one or more flanges and grooves such that the movement of the actuating member 118 relative to the stationary member 116 causes the articulating member 104 to pivot relative to the stationary member 116 into a second, open, position, as shown in FIG. 2B.

Figure 3:
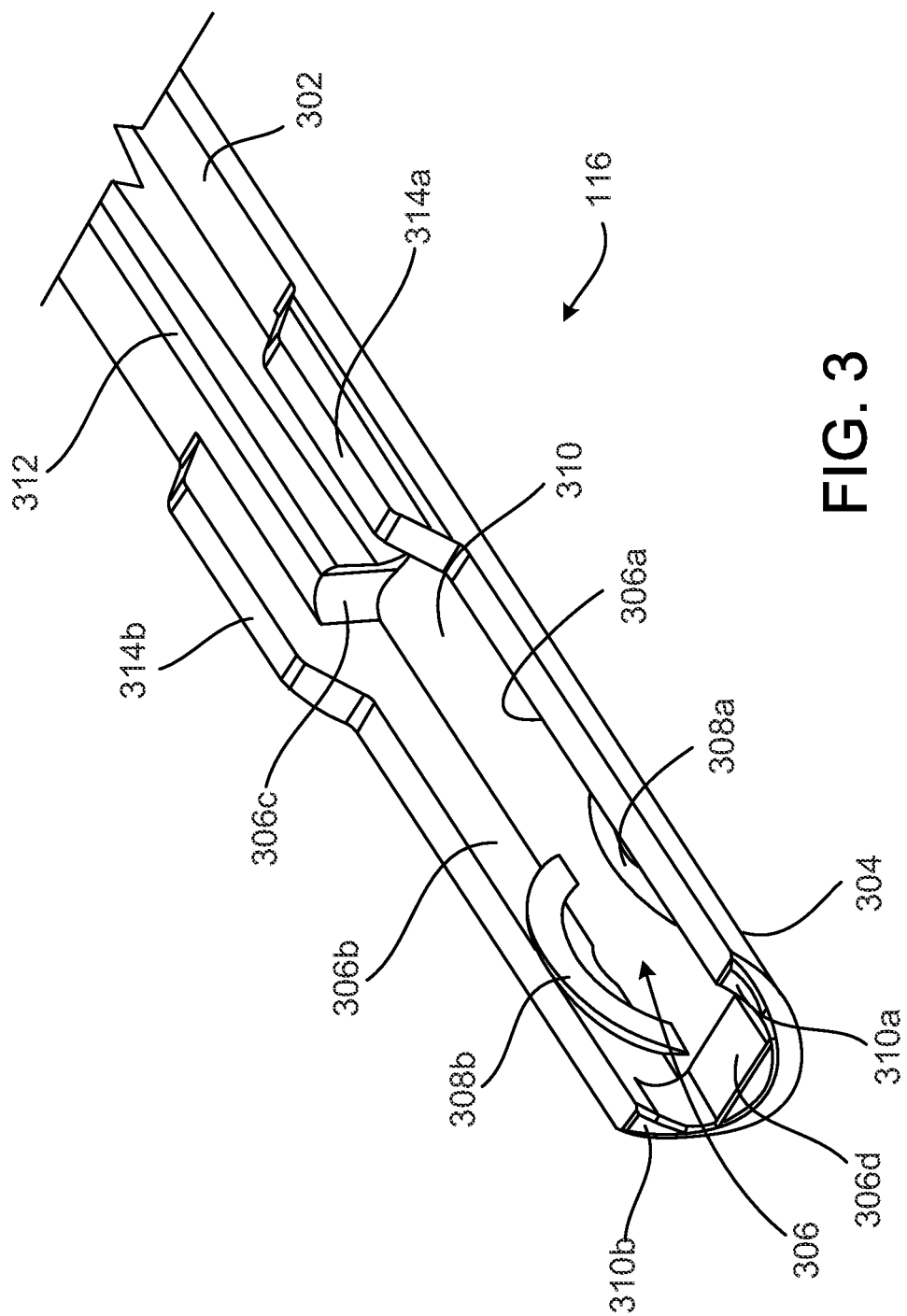
FIG. 3 is a perspective view of the distal end of a stationary member of the surgical guide.

Referring also to FIG. 3, the stationary member 116 is generally semi-circular in cross-section, having a generally flat upper portion 302 and a rounded lower portion 304. A slot 306 is formed in the distal tip of the stationary member 116, and includes sidewalls 306a and 306b connected by an end wall 306c. An opening 310 is formed at the bottom of the slot 306 and extends through the stationary member 116. A connecting member 306d connects the distal ends 310a and 310b of the sidewalls 306a and 306b and may provide structural integrity. The stationary member includes two tabs 314a and 314b.

A first arcuate flange 308a is formed on sidewall 306a. The flange 308a has a center point below the stationary member 116 (that is, the flange 308a is convex when viewed from the upper portion 302 to the lower portion 304). Similarly, a second arcuate flange 308b is located opposite of the arcuate flange 308a on sidewall 306b and has a center point below the stationary member 116. The flanges 308a and 308b are dovetail in shape. A groove 312 runs from the end wall 306c to a proximal end of the stationary member 116.

Figure 4B:
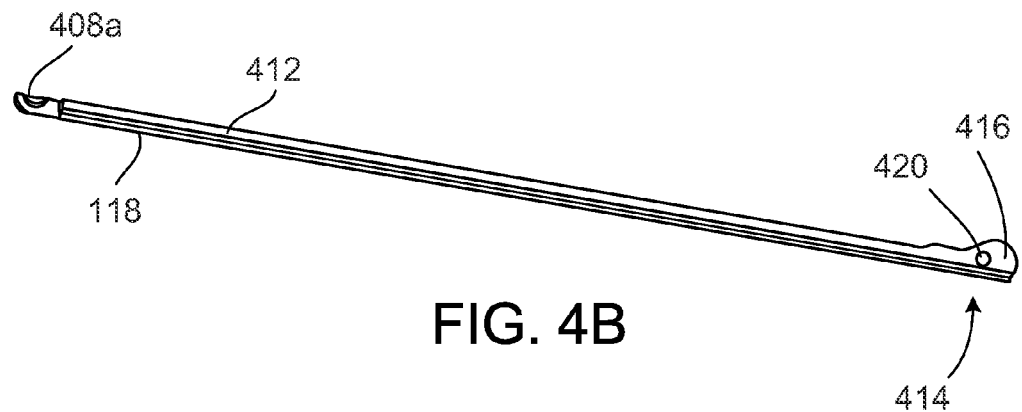
FIG. 4B is a perspective view of a cross-section of the actuating member of the surgical guide.

Referring to FIGS. 4A through 4C, the actuating member 118 is also semi-circular in cross-section, with a generally flat lower portion 402 and a rounded upper portion 404. A notch 406 is formed in the distal tip of the actuating member 118 and extends from the lower portion 402 to the upper portion 404. The notch 406 includes sidewalls 406a and 406b, which are connected by an end wall 406c. The actuating member 118 defines two grooves 418a and 418b on either side of the actuating member 118.

A first arcuate flange 408a is formed on sidewall 406a. The flange 408a has a center point above the actuating member 118 (that is, the flange 408a is concave when viewed from the upper portion 404 to the lower portion 402). Similarly, a second arcuate flange 408b is located opposite of the arcuate flange 408a on sidewall 406b and has a center point above the actuating member 118. Flanges 408a and 408b are dovetail shaped. A groove 412 runs from the end wall 406c to a proximal end 414 of the actuating member 118. The proximal end 414 also includes a flange member 416 that includes a circular opening 420 with a central axis perpendicular to the longitudinal axis of the actuating member 118.

Figure 5:
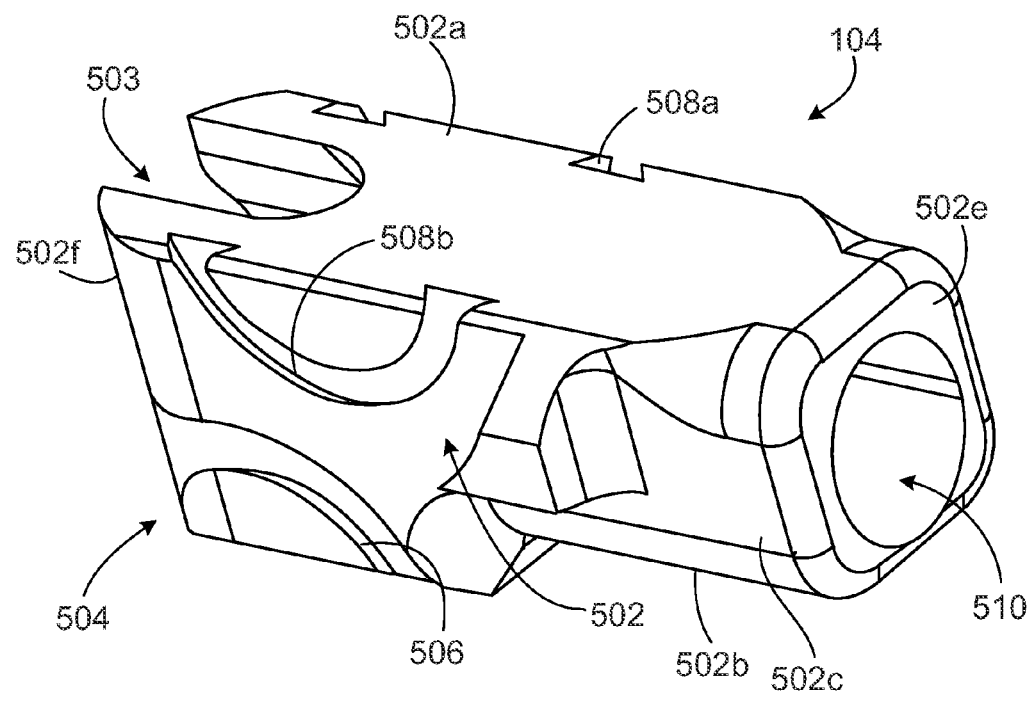
FIG. 5 is a perspective view of the articulating tip of the surgical guide.

Referring to FIG. 5, the articulating member 104 includes a main body 502 and a lower extension portion 504. The main body 502 includes a top 502a, a bottom 502b, a first side 502c, a second side 502d (FIG. 6A), a front 502e, and a back 502f. A lumen 510 extends from the front 502e to the back 502f. The main body 502 defines a notch 503 at the back 502f of the articulating member 104.

The lower extension portion 504 is coupled to a lower portion of the main body 502. The lower extension portion 504 includes a first arcuate groove 506 with a center point below the articulating member 104. The first arcuate groove 506 is shaped to mate with the dovetail arcuate flange on the sidewall 306b of the stationary member 116. A similarly shaped, second arcuate groove (not shown) is formed in the lower extension portion 504 opposite of the first arcuate groove 506. The second arcuate groove is shaped to mate with the dovetail arcuate flange 308a in the sidewall 306a of the stationary member 116.

A third arcuate groove 508a is formed at an upper portion of the main body 502 in the side 502c. The third arcuate groove 508a has a center point above the articulating member 104. The third arcuate groove 508a is shaped to mate with the dovetail arcuate flange 408a on the sidewall 406a of the actuating member 118. A fourth arcuate groove 508b is formed in the side 502d (FIG. 6A) opposite of the third arcuate groove 508a. The fourth arcuate groove 508b is shaped to mate with the dovetail arcuate flange 408b in the sidewall 406b of the actuating member 118.

Figure 6A:
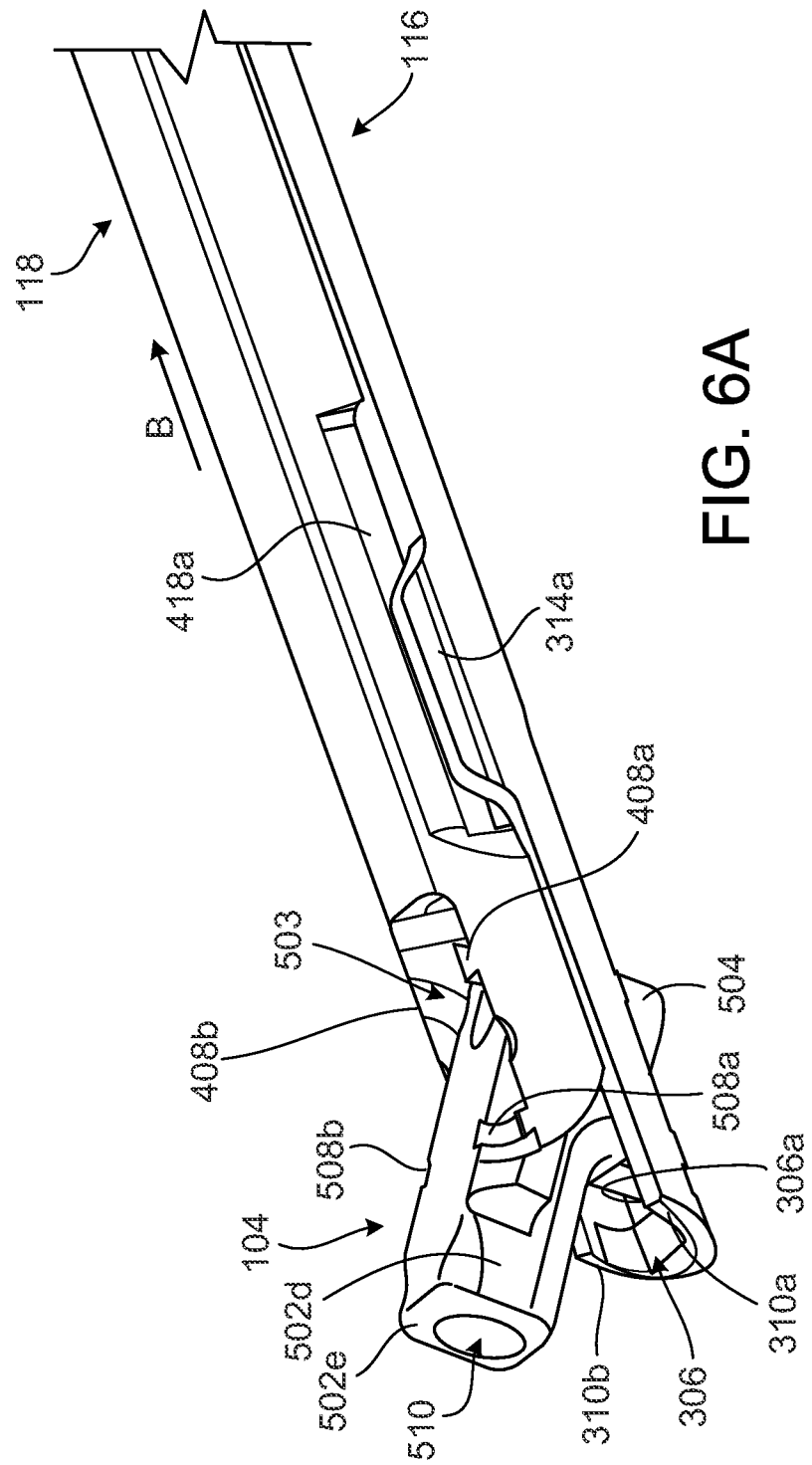
FIGS. 6A and B are perspective views of the distal tip of the surgical guide.
Figure 6B:
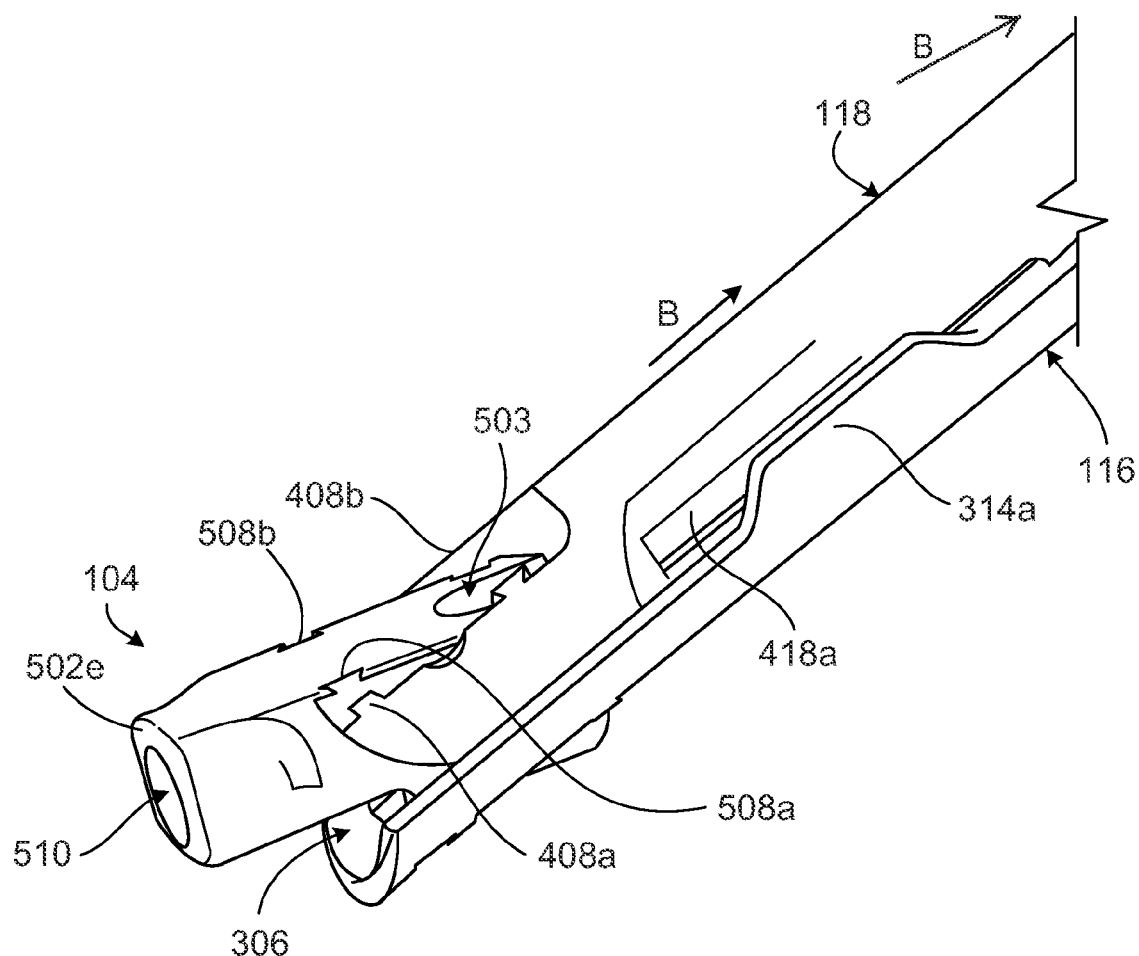
FIGS. 6C and D are plan views of the distal end of the surgical guide.
FIG. 6E is a perspective view of a cross-section of the distal tip of the surgical guide.
Figure 6C:
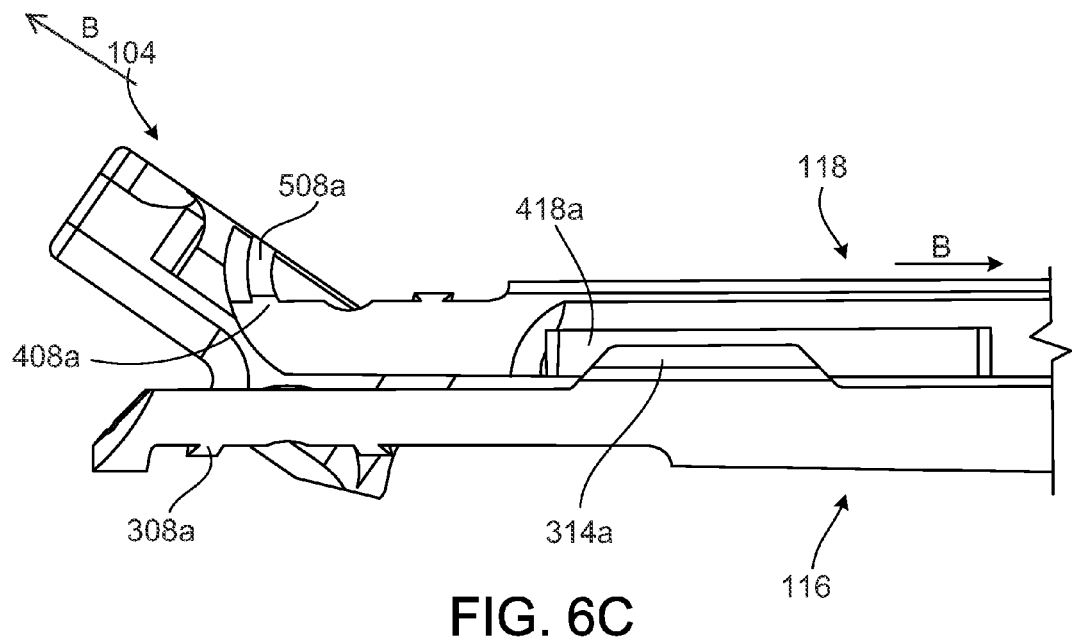

Referring also to FIGS. 6A and 6B, when assembled, the lower extension portion 504 of the articulating member 104 is received in the slot 306 of the stationary member 116. The arcuate grooves on the lower extension portion 504 are mated with the dovetail arcuate flanges on the sidewalls 306a and 306b, with the front 502e of the articulating member facing in the direction of the distal ends 310a and 310b of the sidewalls 306a and 306b. The use of dovetails for the flanges 308a, 308b, 408a, 408b and grooves 506, 508a, 508b may help prevent the separation of the articulating member, the stationary member, and the actuating member during use. The actuating member 118 is arranged so that the flat lower portion 402 of the actuating member 118 faces the flat upper portion 302 of the stationary member 116. Grooves 416a and 416b receive tabs 314a and 314b, respectively. The upper portion of the articulating member 104 is received in the notch 406 of the actuating member 118 and the grooves 508a and 508b on the upper portion are mated with the dovetail arcuate flanges 408a and 408b of the actuating member 118. The groove 312 of the stationary member 116, together with a groove 412 of the actuating member 118, form a lumen that runs the length of the shaft 102. When the articulating member 104 is in a non-pivoted position, the lumen formed by the grooves 312 and 412 is coaxially aligned with the lumen 510 in the articulating member 104. The flexible pin 108 can then be arranged coextensively in both of the lumens, with a distal end 110 of the pin 108 passing out of the front of the articulating member 104.

Figure 6D:
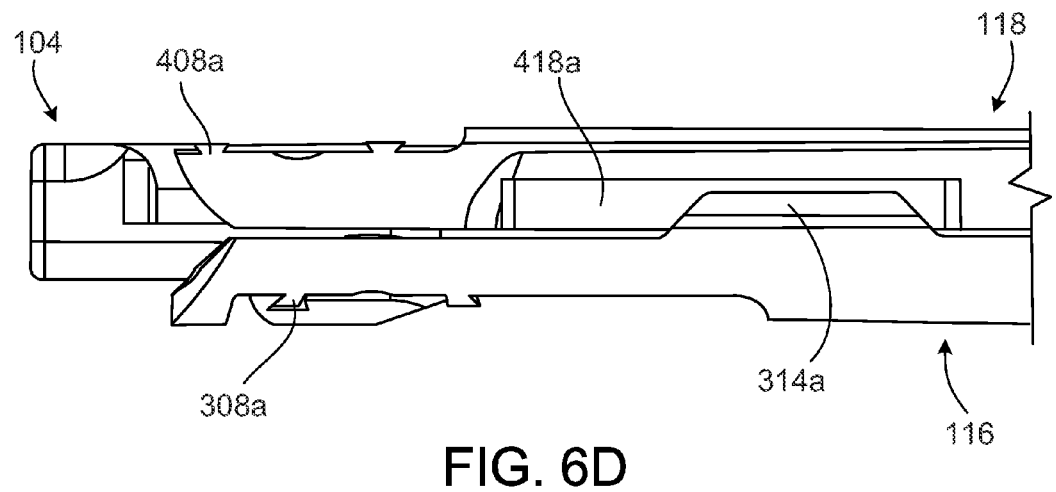
Figure 6E:
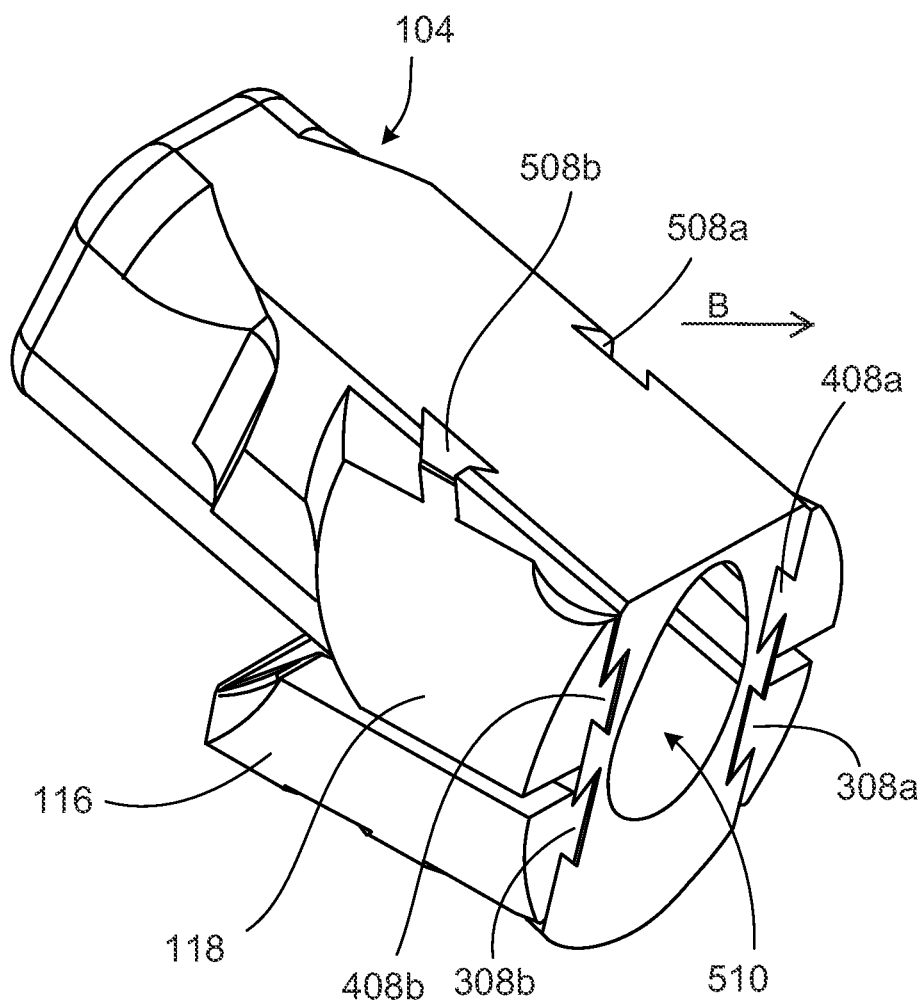

When the actuating member 118 is moved relative to the stationary member 116 in the direction B, the articulating member 104 pivots relative to the stationary member 116 such that an axis of the lumen 510 forms an angle with the axis of the lumen formed by grooves 312 and 412 (as shown in FIGS. 6A, 6B, 6C, and 6E). In other words, the lumens are non-coaxially arranged. When the pin 108 is arranged coextensively in both lumens this non-coaxial arrangement results in the flexible pin 108 bending, as described above. The notch 503 allows the articulating member 104 to rotate without blocking the lumen formed by grooves 312 and 412 or pinching the flexible member 108. The angle between these axes increases as the actuating member 118 is moved further in direction B. When the actuating member 118 is moved in the opposite direction, C, the angle decreases until the angle reaches zero and the articulating member 104 is in a non-pivoted position (as seen in FIG. 6D). The interaction between the tabs 314a and 314b and the grooves 416a and 416b may limit the motion of the actuating member 118 with respect to the stationary member 116, and thereby prevent the dovetail lugs 308a, 308b, 408am and 408b and grooves 508a and 508b from disengaging.

Figure 7A:
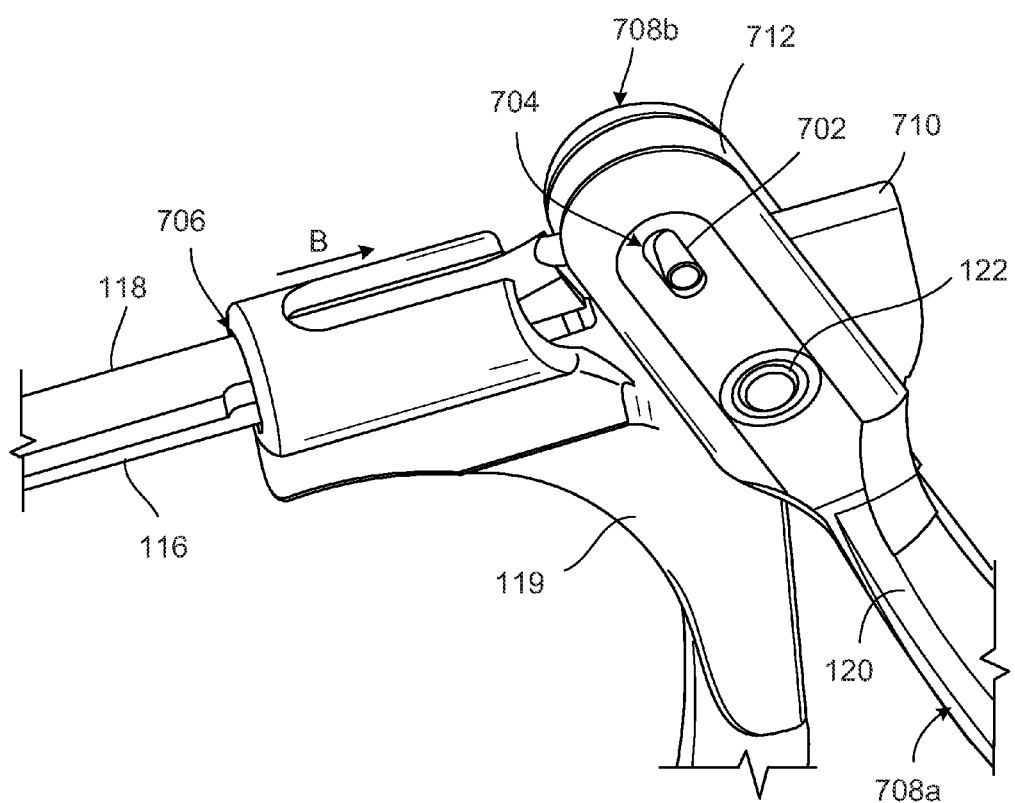
FIG. 7A is a perspective view of a joint of the surgical guide.

Referring to FIG. 7A, when assembled, the upper end 710 of the stationary handle member 119 fits within a slot 712 in the articulating handle member 120 and the two handle members 119 and 120 are coupled with a pin 122, as described above. The flat lower portion 402 of the actuating member 118 contacts the flat upper portion 302 of the stationary member 116, and the two members fit through an aperture 706 in the stationary handle member 119. The actuating member 118 is coupled to the articulating handle member 120 by a pin 702. The pin 702 passes through a slot 704 in the articulating handle member 120 and through the circular opening 420 in the flange member 416 (FIG. 4B). The stationary member 116 is fixed to the stationary handle member 119.

In use, the pin 702 and slot 704 configuration couples the motion of the articulating handle member 120 to the motion of the actuating member 118. When the articulating handle member 120 rotates about pin 122, the lower end 708a of the articulating handle member 120 moves closer to the stationary handle member 119 and the upper end 708b of the articulating handle member 120 moves away from the stationary handle member 119. This rotation causes the actuating member 118 to move towards the proximal end of the device 100, in the direction of B. The converse is also true. When the lower end 708a of the articulating handle member 120 is moved closer to the stationary handle member 119, the upper end 708b of the articulating handle member 120 moves closer to the stationary handle member 119, moving the actuating member 118 farther from the proximal end of the surgical device, opposite the direction of B. The slot 704 allows the pin 702, and hence the actuating member 118, to move along a linear path while the upper end 708b of the articulating handle moves along a circular path.

Figure 7B:
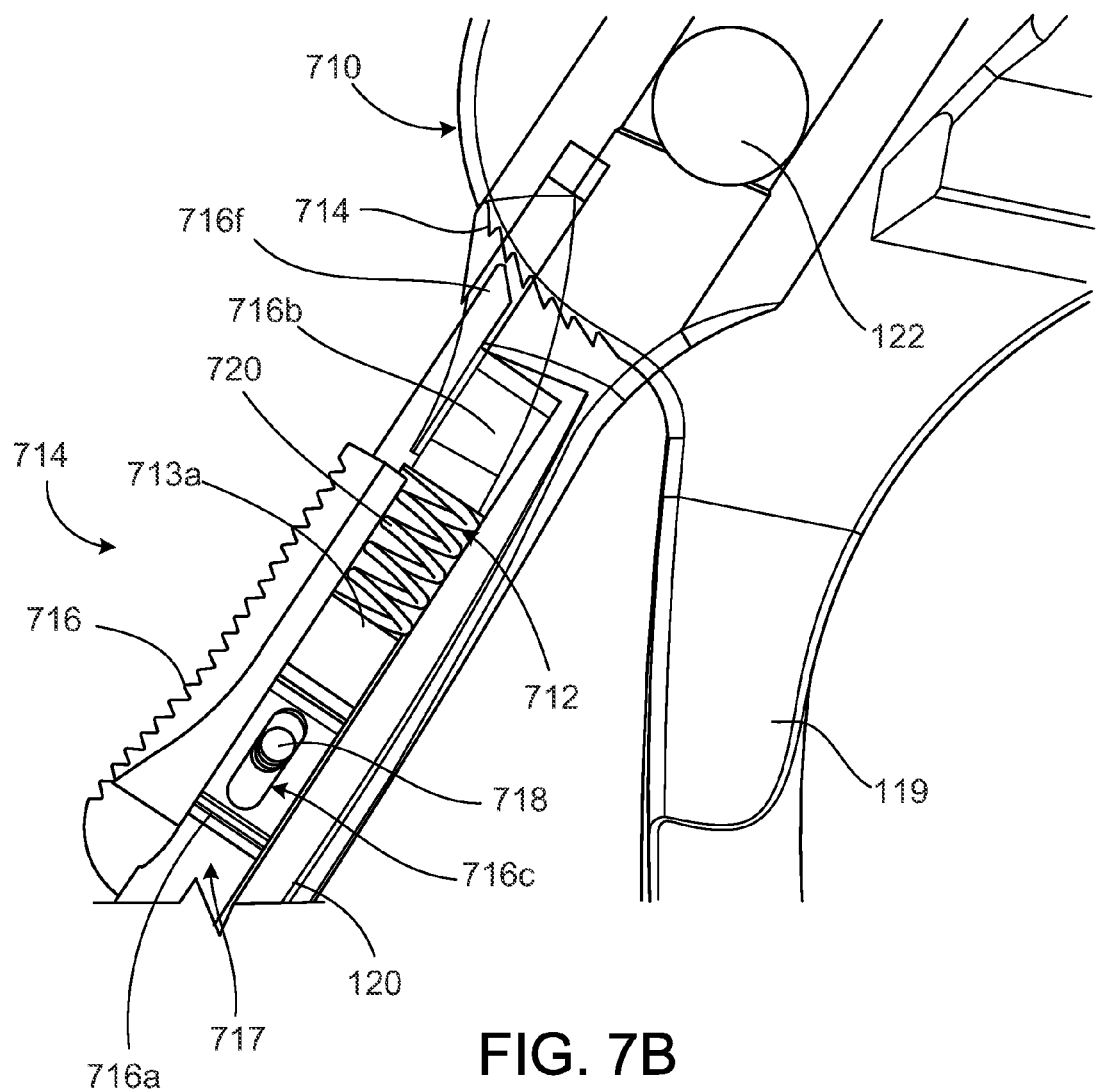
FIG. 7B is a cut-away view of a ratchet mechanism in the handle of the surgical guide.
Figure 7C:
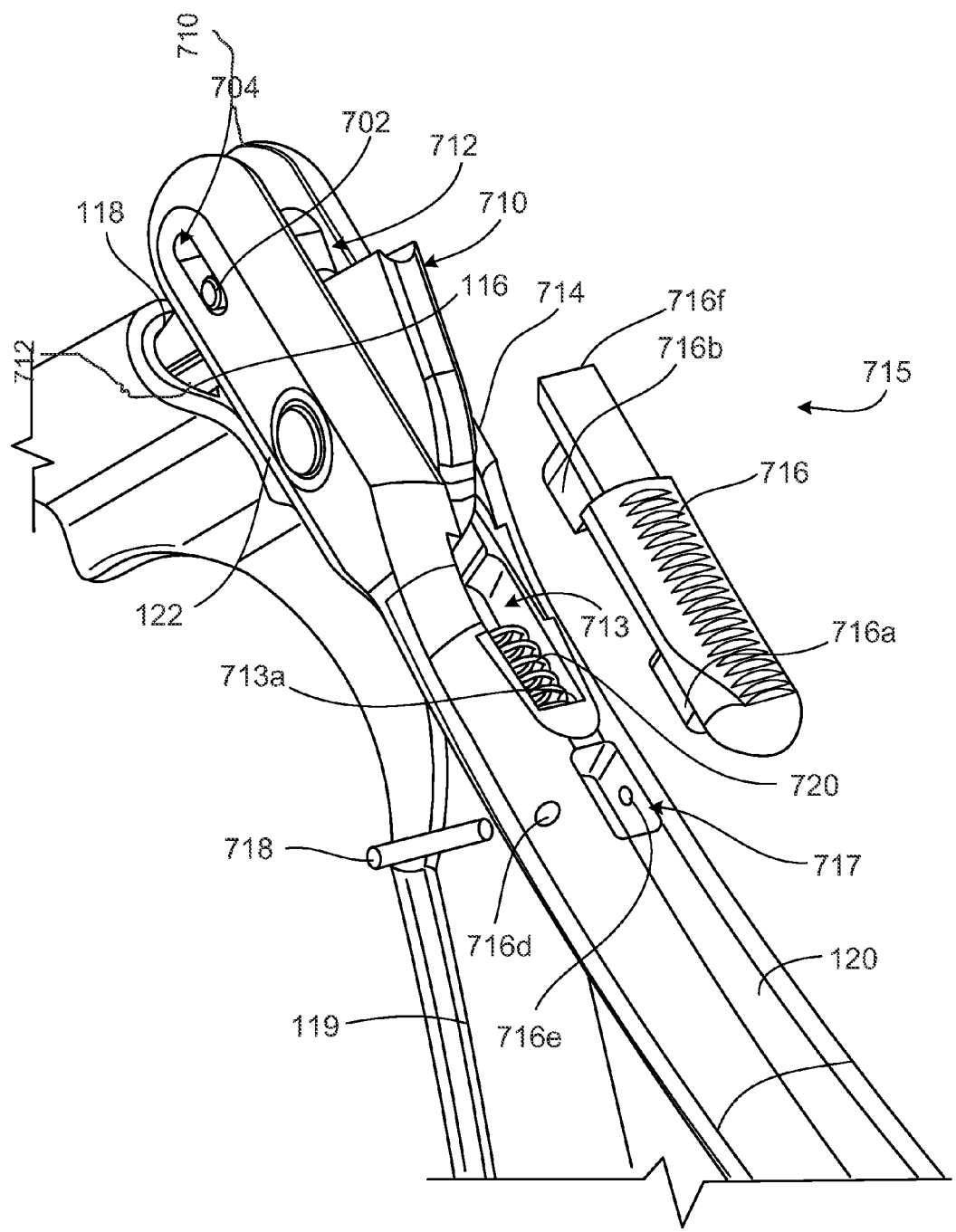
FIG. 7C is a perspective view of the handle of the surgical guide.

Referring now to FIGS. 7B and 7C, the handle 106 includes a ratchet mechanism 715 that allows the articulating handle member 120 to rotate clockwise (when viewed in FIG. 7C) and prevents the articulating handle member 120 from rotating counterclockwise (when viewed in FIG. 7C). The ratchet mechanism 715 comprises a locking mechanism 716, a spring 720, and teeth 714. The teeth 714 are located on the upper end 710 of the stationary handle member 119. The locking mechanism 716 has a finger 716f that is configured to engage with the teeth 714. The locking mechanism 716 also has flanges 716a and 716b that fit into slots 713 and 715, respectively. The slots 713 and 715 are located in the articulating handle member 120. Flange 716a comprises a slot 716c. A locking pin 718 passes through slot 716c and apertures 716d and 716e, which are located on opposing sides of slot 715. The spring 720 is placed within slot 713 between the flange 716b and the backwall 713a of the slot 713.

In use, the locking pin 718 allows the locking mechanism 716 to slide along the longitudinal axis of the articulating handle member 120 while preventing the separation of the locking mechanism 716 and the articulating handle member 120. During surgery, as the surgeon pivots the articulating member 104 by squeezing the handle 106 (causing the articulating handle member 120 to rotate clockwise when viewed in FIG. 7C), the locking mechanism 716 locks the articulating member 104 at the current angle by preventing the articulating handle member 120 from rotating counter-clockwise (when viewed in FIG. 7C). In particular, the finger 716f of the locking mechanism 716 interacts with the teeth 714 on the stationary handle member 119 to lock the motion of the articulating handle member 120 with relation to the stationary handle member 119, thus locking the angle of the articulating member 104 with respect to the stationary member 116. The spring 720 applies a force to the flange 716b, thereby, biasing the locking mechanism 716, and in particular finger 716f, towards the teeth so that the finger 716f engages the teeth 714. The rounded top of the teeth 714 allow the finger 716f of the locking mechanism 716 to slide in one direction, and the opposing flat side of the teeth 714 prevent motion in the other direction, like a ratchet. The locking mechanism 716 can be disengaged from the teeth 714 by manually moving the locking mechanism 716 away from the teeth 714 to release the lock and allow relative motion between the articulating handle member 120 and the stationary handle member 119 in both directions.

FIG. 8 illustrates another implementation of the flexible instrument guide. In this implementation, a ring tube 710 is used to provide stability to the guide in addition, or as an alternative, to the tabs 314a and 314b and the grooves 416a and 416b. The ring tube 710 is positioned around the stationary member 116 and the actuating member 118 at a position proximate to the articulating member 104. The ring tube 710 may provide stability to the guide by preventing the actuating member 118 and the stationary member 116 from twisting during use.

A number of implementations have been described. Nevertheless, it will be understood that various modifications may be made. For example, while the flexible pin guide 100 is shown in use with a knee joint, the guide can be used in other areas of the body, for example a hip or shoulder joint, and would be sized appropriately. In another example, the flanges and grooves may be shaped differently than describe, for example in a dovetail shape. A ratchet type mechanism has been described, but other locking methods, such as securing the location with a pin, using a clamp to secure the handles, etc. are also contemplated. The handle 106 may also include markings to indicate the angle or position of the articulating member 104 with respect to a reference such as the stationary member 116. The articulating member 104 may be curved. The lumen 510 within the articulating member 104 may be curved. Accordingly, other implementations are within the scope of the following claims.

The invention claimed is:

1. A guide comprising:
a handle that defines a first handle member and a second handle member, the second handle member configured to move with respect to the first handle member;
an elongate shaft that defines a proximal end and a distal end, the elongate shaft coupled to the handle on the proximal end of the elongate shaft, and the elongate shaft comprising:
a stationary member that defines a proximal end and a distal end, the proximal end of the stationary member coupled to and stationary with respect to the first handle member;
a slot defined in the distal end of the stationary member, the slot defines a first sidewall and a second sidewall opposite the first sidewall;
a first arcuate flange disposed on the first sidewall, wherein the first arcuate flange has a center point below the stationary member;
a first groove defined in the stationary member, the groove extends from the slot to the proximal end of the stationary member;
an actuating member that defines a proximal end and a distal end, the proximal end of the actuating member coupled to and movable by the second handle member, and the actuating member abutting the stationary member;
a notch defined in the distal end of the actuating member, the notch defines a first sidewall and a second sidewall opposite the first sidewall of the notch;
a second arcuate flange disposed on the first sidewall of the notch, wherein the second arcuate flange has a center point above the actuating member;
a second groove defined by the actuating member, the second groove extends from the notch to the proximal end of the actuating member;
an articulating member that defines a first lumen and two sides, the articulating member disposed within the slot of the stationary member and the notch of the actuating member;
a first arcuate groove defined in a side of the articulating member, the first arcuate groove disposed over the first arcuate flange of the stationary member;
a second arcuate groove defined in a side of the articulating member, the second arcuate grooves disposed over the second arcuate flange of the actuating member; and
wherein the stationary member, the articulating member, and the actuating member are coupled to one another such that the articulating member is configured to pivot relative to the stationary member when the actuating member is moved relative to the stationary member; and
wherein the first and second grooves form a second lumen arranged to accommodate a flexible member coextensively in the first lumen and the second lumen.

2. The guide of claim 1 wherein the stationary member, the articulating member, and the actuating member are coupled such that the first lumen and the second lumen are coaxially arranged when the actuating member is in a first position relative to the stationary member and are non-coaxially arranged when the actuating member is in a second position relative to the stationary member.

3. The guide of claim 1 wherein the handle comprises a pin coupling the first handle member and the second handle member such that the second handle member rotates relative to the first handle member.

4. The guide of claim 1 wherein the handle includes a ratchet mechanism configured to allow the second handle member to rotate in a first direction and configured to prevent the second handle member from rotating in a second direction, opposite the first direction.

5. The guide of claim 4 wherein rotation in a first direction moves the actuating member from a first position to a second position.

6. The guide of claim 4 wherein the ratchet mechanism includes one or more teeth on the first handle member and a finger on the second handle member, the finger configured to engage the teeth.

7. The guide of claim 6 wherein the finger is configured to move in a first direction to engage the teeth and to move in a second direction to disengage the teeth, the ratchet mechanism comprising a spring configured to apply a force to the finger in the first direction to engage with the teeth and allow the finger to be moved in the second direction to disengage the finger from the teeth.

8. A guide comprising:
   a handle that defines a first handle member and a second handle member, the second handle member configured to move with respect to the first handle member;
   an elongate shaft that defines a proximal end and a distal end, the elongate shaft coupled to the handle on the proximal end of the elongate shaft, and the elongate shaft comprising:
      a stationary member that defines a proximal end and a distal end, the proximal end of the stationary member coupled to and stationary with respect to the first handle member;
      a slot defined in the distal end of the stationary member, the slot defines a first sidewall and a second sidewall opposite the first sidewall;
      a first arcuate flange and a second arcuate flange disposed on the first and second sidewalls, respectively, wherein each arcuate flange has a center point below the stationary member;
      a first groove defined in the stationary member, the groove extends from the slot to the proximal end of the stationary member;
      an actuating member that defines a proximal end and a distal end, the proximal end of the actuating member coupled to and movable by the second handle member, and the actuating member abutting the stationary member;
      a notch defined in the distal end of the actuating member, the notch defines a first sidewall and a second sidewall opposite the first sidewall of the notch;
      a third arcuate flange and a fourth arcuate flange disposed on the first and second sidewalls of the notch, respectively, wherein each of the third and fourth arcuate flange has a center point above the actuating member;
      a second groove defined by the actuating member, the second groove extends from the notch to the proximal end of the actuating member;
      an articulating member that defines a first lumen, a first side and a second side opposite the first side, the articulating member disposed within the slot of the stationary member and the notch of the actuating member;
      a first arcuate groove and a second arcuate groove defined in the first and second sides of the articulating member, respectively, the first and second arcuate grooves disposed over the first and second arcuate flanges of the stationary member, respectively;
      a third arcuate groove and a fourth arcuate groove defined in the first and second sides of the articulating member, respectively, the third and fourth arcuate grooves disposed over the third and fourth arcuate flanges of the actuating member, respectively; and
   wherein the stationary member, the articulating member, and the actuating member are coupled to one another such that the articulating member is configured to pivot relative to the stationary member when the actuating member is moved relative to the stationary member; and
   wherein the first and second grooves form a second lumen arranged to accommodate a flexible member coextensively in the first lumen and the second lumen.

9. An instrument guide comprising:
   a handle that defines a first handle member and a second handle member, the second handle member configured to move with respect to the first handle member;
   an elongate shaft that defines a proximal end and a distal end, the elongate shaft coupled to the handle on the proximal end of the elongate shaft, and the elongate shaft comprising:
      a stationary member that defines a proximal end and a distal end, the proximal end of the stationary member coupled to and stationary with respect to the first handle member;
      a slot defined in the distal end of the stationary member, the slot defines a first sidewall and a second sidewall opposite the first sidewall;
      a first groove defined in the stationary member, the groove extends from the slot to the proximal end of the stationary member;
      an actuating member that defines a proximal end and a distal end, the proximal end of the actuating member coupled to and movable by the second handle member, and the actuating member abutting the stationary member;
      a notch defined in the distal end of the actuating member, the notch defines a first sidewall and a second sidewall opposite the first sidewall of the notch;
      a second groove defined by the actuating member, the second groove extends from the notch to the proximal end of the actuating member;
      an articulating member that defines a first lumen, a first side and a second side opposite the first side, the articulating member disposed within the slot of the stationary member and the notch of the actuating member;
      a means for rotationally coupling the articulating member to the stationary member;
      a means for rotationally coupling the articulating member to the actuating member;
   the stationary member, the articulating member, and the actuating member are coupled to one another such that the articulating member is configured to pivot relative to the stationary member when the actuating member is moved relative to the stationary member; and
   the first and second grooves form a second lumen arranged to accommodate a flexible pin coextensively in the first lumen and the second lumen.

10. The instrument guide of claim 9 wherein the means for rotationally coupling the articulating member to the stationary member further comprises:
    a first arcuate flange and a second arcuate flange disposed on the first and second sidewalls of the slot, respectively, and wherein each arcuate flange has a center point below the stationary member; and
    a first arcuate groove and a second arcuate groove defined in the first and second sides of the articulating member, respectively, the first and second arcuate grooves disposed over the first and second arcuate flanges of the stationary member, respectively.

11. The instrument guide of claim 10 wherein the means for rotationally coupling the articulating member to the actuation member further comprises:
    a third arcuate flange and a fourth arcuate flange disposed on the first and second sidewalls of the notch, respectively, wherein each of the third and fourth arcuate flange has a center point above the actuating member; and a third arcuate groove and a fourth arcuate groove defined in the first and second sides of the articulating member, respectively, the third and fourth arcuate grooves disposed over the third and fourth arcuate flanges of the actuating member, respectively.

12. The instrument guide of claim 9 wherein the means for rotationally coupling the articulating member to the actuation member further comprises:

a first arcuate flange and a second arcuate flange disposed on the first and second sidewalls of the notch, respectively, wherein each of the first and second arcuate flange has a center point above the actuating member; and a first arcuate groove and a second arcuate groove defined in the first and second sides of the articulating member, respectively, the first and second arcuate grooves disposed over the first and second arcuate flanges of the actuating member, respectively.

* * * * *